United States Patent [19]
Mukherjee et al.

[11] Patent Number: 5,763,979
[45] Date of Patent: Jun. 9, 1998

[54] ACTUATION SYSTEM FOR THE CONTROL OF MULTIPLE SHAPE MEMORY ALLOY ELEMENTS

[75] Inventors: Ranjan Mukherjee, Lansing, Mich.; Thomas F. Christian, Pacific Grove, Calif.

[73] Assignee: The United States of America as represented by the Secretary of the Navy, Washington, D.C.

[21] Appl. No.: 808,721

[22] Filed: Feb. 28, 1997

Related U.S. Application Data

[60] Provisional application No. 60/012,586, Feb. 29, 1996.
[51] Int. Cl.$^6$ ............................................. H02N 10/00
[52] U.S. Cl. ......................... 310/306; 337/140; 318/117
[58] Field of Search ............................. 337/111, 140, 337/379, 393; 310/306, 307; 318/116, 117

[56] References Cited

U.S. PATENT DOCUMENTS

| | | | |
|---|---|---|---|
| 4,265,601 | 5/1981 | Mandroian | 417/379 |
| 4,732,556 | 3/1988 | Chiang et al. | 425/405.2 |
| 4,753,223 | 6/1988 | Bremer | 604/95 X |
| 4,868,448 | 9/1989 | Kornrumpf | 310/331 |
| 4,987,314 | 1/1991 | Gotanda et al. | 250/551 |
| 5,279,559 | 1/1994 | Barr | 604/95 |
| 5,389,072 | 2/1995 | Imran | 604/95 |
| 5,405,337 | 4/1995 | Maynard | 604/281 |
| 5,531,677 | 7/1996 | Lundquist et al. | 604/22 |

OTHER PUBLICATIONS

A LinearSMA Motor as Direct-Drive Robotic Actuator by M. Bergamasco et al., pp. 618–623, 1989 Proc. IEEE International Conference on Robotics and Automation (Month Unkown).

A Miniature Device for Medical Intracavity Intervention by Paolo Dario et al., pp. 171–175, 1991 Proc. IEEE International Conference on Robotics and Automation (Month Unknown).

Micro Active Catheter System With Multi Degrees of Freedom by Toshio Fukuda et al., pp. 2290–2295, 1994 Proc. IEEE Conference on Robotics and Automation (Month Unknown).

Micro/Miniature Shape Memory Alloy Actuator by Koji Ikuta, pp. 2156–2161, 1990 IEEE International Conference on Robotics and Automation (Monthe Unknown).

Shape Memory Alloy Servo Actuator System With Electric Resistance Feedback and Application for Active Endoscope by Koji Ikuta et al., pp. 427–430, 1988 IEEE International Conference on Robotics and Automation (Month Unknown).

A New Actuator of a Joint Mechanism Using TiNi Alloy Wire by Katsutoshi Kuribayashi, pp. 44–58, The International Journal of Robotics Research, vol. 4, No. 4, Winter 1986 (Month Unknown).

Millimeter–Sized Joint Actuator Using a Shape Memory Alloy by Katsutoshi Kuribayashi pp. 57–64, Sensors and Actuators, 20 (1989) (Month Unknown).

An Introduction to Martensite Shape Memory by C.M. Wayman et al., pp. 3–20, Engineering Aspects of Shape Memory Alloys, (1990 Month Unknown).

*Primary Examiner*—Steven L. Stephan
*Assistant Examiner*—Judson H. Jones
*Attorney, Agent, or Firm*—Donald E. Lincoln

[57] ABSTRACT

An actuation system for the control of multiple shape memory alloy elements is achieved by arranging the shape memory actuators into a matrix comprised of rows and columns which results in approximate a fifty percent reduction in the number of electrical connecting wires. This method of actuation provides the scope for resistance measurements of the shape memory alloy actuators and therefore feedback control of the actuators can be accomplished without additional wires.

4 Claims, 2 Drawing Sheets

ACTUATION SYSTEM FOR THE CONTROL OF MULTIPLE SHAPE MEMORY ALLOY ELEMENTS

BACKGROUND OF THE INVENTION

1. Field of the Invention

This invention relates to the use of Shape Memory Alloys (SMA) as actuators.

2. Description of the Related Art

Shape Memory Alloys (SMA) possess shape memory when heated. The mechanism of shape memory is based on the complex transformation of the material between martensite and austenite. The solid state transformation from austenite to martensite is displacive, athermal (time independent), first order (liberates heat), associated with a hysteresis and occurs over a temperature span in which both phases exist (C. M. Wayman and T. W. Duerig, "An Introduction to Martensite and Shape Memory", Engineering Aspects of Shape Memory Alloys, pp. 3–20, Eds. T. W. Duerig, K. N. Melton, D. Stockel, and C. M. Wayman, Butterworth-Heinemann, Boston, Mass.). Through Bain strain and lattice invariant shear, the austenite structure is transformed upon cooling into a twinned martensite with little volume change. Detwinning the martensite results in a significant shape change of approximately 4 to 8% deformation. This deformation is fully recoverable, provided that the applied stress level has not produced slip, when the material is heated and the austenite has fully formed. The austenite forms completely at the austenite finish temperature, $A_f$, which is determined by the atomic percentages of the alloying elements in the Shape Memory Alloy.

An SMA actuator is activated by raising the temperature of the alloy above its austenite finish temperature $A_f$ (C. M. Wayman and T. W. Duerig, "An Introduction to Martensite and Shape Memory", Engineering Aspects of Shape Memory Alloys, pp. 3–20, Eds. T. W. Duerig, K. N. Melton, D. Stockel, and C. M. Wayman, Butterworth-Heinemann, Boston, Mass.). The alloy is initially in its martensite phase when heating of the alloy results in an increase in its temperature. At an elevated temperature $A_s$, the alloy begins to transform from martensite to austenite and the transformation is completed at the temperature $A_f > A_s$. If the SMA actuators are heated electrically and controlled in the open loop, the number of connecting wires required is one more than the number of actuators—one common ground and one wire for each individual actuator. If closed loop control of the SMA actuators is desired, the number of connecting wires required would be even higher unless resistance measurement is used for feedback (K. Ikuta, M. Tsukamoto and S. Hirose, "Shape Memory Alloy Servo Actuator System with Electric Resistance Feedback and Application for Active Endoscope", 1988 IEEE International Conference on Robotics and Automation, pp. 427–430)). As the alloy transforms from martensite to austenite, the resistance of the alloy decreases sharply and this change can be monitored for the feedback control of the SMA actuator from martensite to austenite. The resistance of an SMA actuator can be monitored by using the same wires that are used to heat it electrically—this eliminates the necessity of additional wires.

Shape Memory Alloys (SMA) are often used as actuators in articulated miniature devices. For example, SMA helical springs were used as actuators in the phalangeal structure of a robotic finger by M. Bergamasco, F. Salsedo and P. Dario ("Shape Memory Alloy Micromotors for Direct-Drive Actuation of Dexterous Artificial Hands", Sensors and Actuators, pp. 115–119, 1989), an active catheter tip actuated by annealed SMA elements was designed for medical intercavity intervention by P. Dario, R. Valleggi, M. Pardini and A. Sabatini ("A Miniature Device for Medical Intracavitary Intervention", 1991 IEEE International Conference on Robotics and Automation, pp. 171–175), a micro active catheter with embedded SMA actuating elements was developed and tested by T. Fukuda, S. Guo, K. Kosuge, F. Arai, M. Negoro and K. Nakabayashi ("Micro Active Catheter System with Multi Degrees of Freedom", 1994 IEEE International Conference on Robotics and Automation, pp. 2290–2295) and Shape Memory Alloy servo actuators were used for the development of an active endoscope by K. Ikuta, M. Tsukamoto and S. Hirose ("Shape Memory Alloy Servo Actuator System with Electric Resistance Feedback and Application for Active Endoscope", 1988 IEEE International Conference on Robotics and Automation, pp. 427–430). These devices typically use multiple actuators to achieve multiple degrees of articulation. The actuators are usually activated by electrical current which conventionally requires more connecting wires than the number of actuators. Due to space constraints, the number of degrees of articulation of a miniature device is limited by the total number of electrical connecting wires that may be accommodated in the device.

Articulated devices, such as an active endoscope having multiple degrees of freedom, often use multiple Shape Memory Alloy active elements. In the conventional method of actuation, the number of electrical wires required is one more than the number of actuators. Since the number of wires that may be accommodated in a miniature device is limited due to space constraints, the conventional method of actuation limits the number of SMA elements or the number of degrees of freedom a miniature device may have.

SUMMARY OF THE INVENTION

The present invention addresses this problem by reducing the number of connecting wires required for the activation of multiple SMA actuators. The actuation technique also provides the scope for the closed loop control of the actuators using resistance feedback. This invention's method of actuation requires fewer electrical wires than the conventional method. For example, this invention's method requires 8 wires to activate 15 SMA actuators which conventionally requires 16 wires. This is a 50% reduction in the number of connecting wires. It should also be mentioned that the present method of actuation provides the scope for resistance measurements of the SMA actuators and therefore feedback control of the actuators can be accomplished without additional wires.

Therefore, it is an object of the present invention to reduce the number of electrical connecting wires required for the actuation of multiple Shape Memory Alloy (SMA) elements and provide a method for the actuation of the elements. In the preferred embodiment, the SMA actuators are arranged as elements of a matrix. The SMA actuators are individually heated electrically by using a pulsed matrix composed of rows and columns. The number of rows and the number of columns are determined by the number of SMA elements to be actuated. Each of the SMA actuators is digitally selected and individually heated by a high current pulse for a short duration of time. In the preferred embodiment, the SMA elements are heated by a current pulse whose amplitude and duration are both variables. The actuators are sequentially selected and heated cyclically with each actuator being pulsed only once in every cycle. A computer digitally selects an individual element of the matrix by energizing two solid state switches—one driving the row and the other driving the columns containing the individual SMA actuator.

It is a further object of this invention to provide other methods of actuating the SMA elements. One alternative method is to maintain the magnitude of the current pulse at a fixed level and change the duration of the pulse. Another alternative method is to maintain the duration of the current pulse and vary the magnitude of the pulse. Another method of actuating the SMA elements is to use a separate "free running" timer interface, synchronized to the voltage sensing multiplexer and the actuator selection circuitry, to drive the on and off periods.

DESCRIPTION OF THE INVENTION

Figure 1:
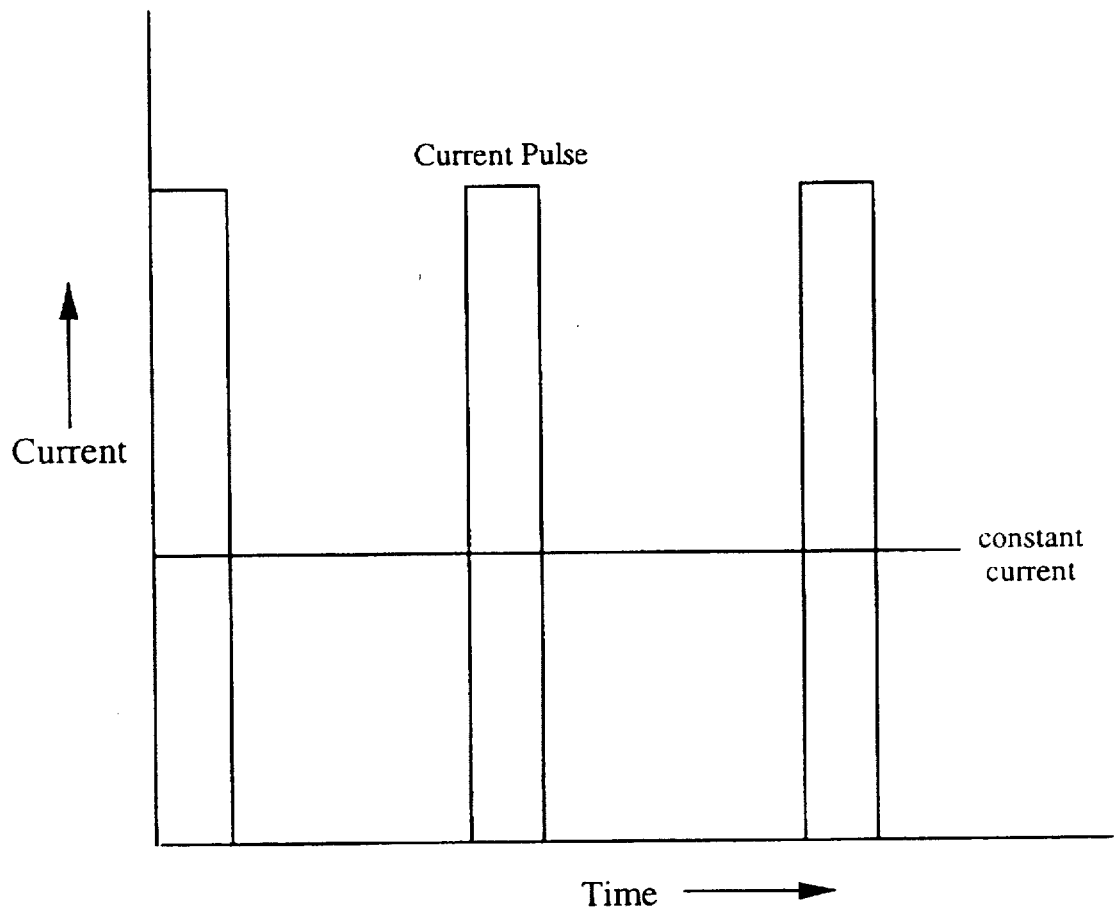
FIG. 1 illustrates the heating cycle of alternate short current pulses and relatively long periods of no current.

The phase transformation of an SMA element from martensitic to austenite is commonly induced by electrical heating. In the conventional method of actuation, each SMA element is continuously heated. The current required to heat an SMA element to a temperature above the austenite finish temperature $A_f$, and maintain it at that temperature, can be obtained from the heat transfer equation $$mc_p\left(\frac{dT}{dt}\right) = \dot{Q}_i - \dot{Q}_o \quad (1)$$
$$= i^2R - hA(T - T_\infty)$$

where:

m is the mass of the SMA element, $c_p$ is the specific heat of the element,

T is the instantaneous temperature of the element in Kelvin, $T_\infty$ the ambient temperature in Kelvin, $\dot{Q}_i$ is the rate of energy input to the element, $\dot{Q}_o$ is the rate of energy loss from the element due to heat transfer, i is the current in the element, R is the resistance of the element, h is the coefficient of convective heat transfer and A is the surface area of the SMA element.

At steady state the temperature in the SMA element reaches a constant value; the current required to achieve this constant temperature can be computed as $$i_c = \sqrt{hA(T - T_\infty)/R} \quad (2)$$

An SMA exhibits a substantial difference in its resistance between the austenitic and the martensitic phases (K. Ikuta, M. Tsukamoto and S. Hirose, "Shape Memory Alloy Servo Actuator System with Electric Resistance Feedback and Application for Active Endoscope", 1988 IEEE International Conference on Robotics and Automation, pp. 427-430)). Since the SMA element will be in its austenitic phase at steady state, the resistance of the SMA in the austenitic phase should be used as the value of R to compute the current in Eq. (2).

Now consider the possibility of discontinuously heating the element using a cycle of alternate short current pulses and relatively long periods of no current. This is diagrammatically shown in FIG. 1. This mode of discontinuous heating will eventually cycle the temperature of the wire between two different temperatures—let these temperatures be $T_1$ and $T_2$, with $T_1$ denoting the higher temperature. The discontinuous method of heating the SMA elements will be feasible provided the SMA remains in its austenite phase all throughout the duty cycle—this will require that the temperature $T_2$ be higher than the austenite finish temperature $A_f$.

Let us assume that the duty cycle spans nγ seconds with the current on for γ seconds and off for the rest of the time. When the current is on, the temperature of the wire changes in accordance with Eq.(1), the solution of which is given as $$(T - T_\infty) = \frac{i^2R}{hA} + Ce^{-\Lambda t/\gamma}, \quad \Lambda \triangleq \frac{hA\gamma}{mc_p} \quad (3)$$

where C is a constant of integration. Since the temperature of the wire cycles between $T_2$ and $T_1$, the two boundary conditions are: $T=T_2$ at t=0, and $T=T_1$ at t=γ.

Substitution of these conditions in Eq.(3) gives us the identity $$(T_1 - T_\infty) = (T_2 - T_\infty)e^{-\Lambda} + \frac{i^2R}{hA}(1 - e^{-\Lambda}) \quad (4)$$

In the period following the heating, the temperature of the wire will decrease from $T_1$ to $T_2$, and the decrease in the wire temperature will be governed by the differential equation $$mc_p\left(\frac{dT}{dt}\right) = -hA(T - T_\infty) \quad (5)$$

Substitution of the boundary conditions: $T=T_1$ at t=0, and $T=T_2$ at t=(n−1)γ results in the second identity $$(T_2 - T_\infty) = (T_1 - T_\infty)e^{-\Lambda(n-1)} \quad (6)$$

By substituting Eq.(6) in Eq.(4) to eliminate the variable $T_1$, we arrive at the expression relating the current i to the temperature $T_2$, given below $$i = \sqrt{\frac{hA}{R}(T_2 - T_\infty)\left[\frac{e^{\Lambda n} - 1}{e^{\Lambda} - 1}\right]} \quad (7)$$

Equation (7) enables us to understand how we can exploit the thermal inertia of the SMA element during discontinuous heating. Specifically, it tells us:

1. If the duration of the current pulse, γ, is a constant, (then the parameter $\Lambda$ defined by Eq.(3) is also a constant), and the integer n is a constant, then the temperature $T_2$ can be increased by increasing the current, i. It may be necessary to increase $T_2$ if it is less than $A_f$ or not sufficiently above $A_f$.

2. In practical situations γ will be of the order of 10 milliseconds, and therefore the parameter $\Lambda$ will be quite small. The integer n will have a typical value of 10 and therefore $\Lambda$n will be greater than $\Lambda$ by an order of magnitude. This motivates us to truncate $e^{-\Lambda}$ after its second term and $e^{-\Lambda n}$ after its third term, as we expand both of them in power series. Subsequently, Eq.(7) simplifies to the form $$i = \sqrt{\frac{hA}{R}(T_2 - T_\infty)n\left(1 + \frac{1}{2}\Lambda n\right)} \quad (8)$$

Equation (8) tells us that the temperature $T_2$ can be increased without increasing the current i, by decreasing the value of n which is intuitive, or by decreasing the value of Λ which can be achieved by decreasing the value of γ. Experimental results presented in the Alternatives section will demonstrate that γ can be decreased to increase the temperature $T_2$.

3. If the duration of the current pulse is made very small, such that both Λ and Λn are small, then Eq.(8) further simplifies to $$i = \sqrt{\frac{nhA}{R}(T_2 - T_\infty)} = \sqrt{n}\, i_c \qquad (9)$$

where $i_c$ was defined in Eq. (2). Eq. (9) tells us that for very small values of γ, the relation between the current i and the temperature $T_2$ is independent of γ. In other words, γ cannot be indefinitely decreased to increase the temperature $T_2$ for a constant magnitude of the current.

The number n represents the total number of SMA active elements that will be actuated. While the method of actuation will be discussed next, we wish to mention here that each of the SMA elements will be actuated individually and sequentially by a short current pulse. The current pulse will be switched from one SMA element to the next in a sequential fashion. Consequently, each element will be heated for x seconds in a duty cycle of duration nx seconds.

In our method of actuation, the Shape Memory Alloy (SMA) actuators are individually heated electrically by using a pulsed matrix composed of rows and columns FIG. 1. The number of rows and the number of columns are determined by the number of SMA elements to be actuated. Each of the SMA actuators is digitally selected and individually heated by a high current pulse for a short duration of time. The actuators are sequentially selected and heated cyclically with each actuator being pulsed only once in every cycle.

The SMA actuators are arranged as elements of a matrix. A computer digitally selects an individual element of the matrix by energizing two solid state switches—one driving the row and the other driving the column containing the individual SMA actuator. A digital to analog convertor, driving a constant current high speed pulse amplifier, generates a high current pulse of electrical energy into the selected actuator. The resistance of the actuator can be calculated using Ohm's law from the magnitude of the programmed current pulse and the voltage sampled across the actuator. Each actuator is calibrated for resistance versus temperature ahead of time. This information is used to adjust the amplitude of the current pulse in a closed loop fashion to heat the actuator up to the proper temperature. The pulse width and repetition rate is dependent on the number of SMA actuators that are heated simultaneously.

Figure 2:
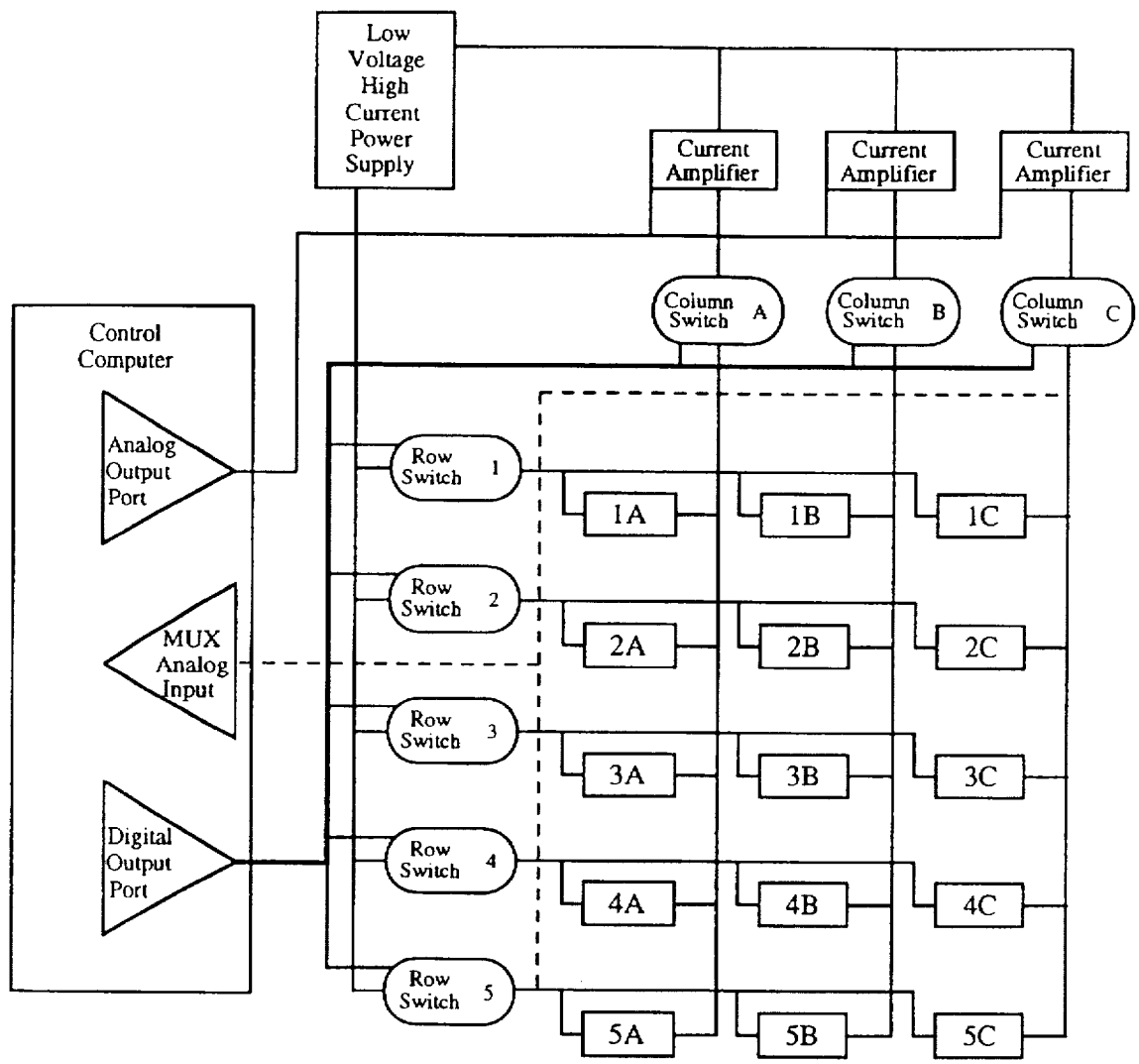
FIG. 2 illustrates a set of 15 SMA actuators arranged in the form of a 3×5 matrix.

To better describe our invention, we now consider a set of 15 SMA actuators that we arrange in the form of a matrix of size 3×5, see FIG. 2. The columns are marked A, B and C, and the rows are marked 1, 2, 3, 4 and 5. Each SMA element can therefore be denoted by the alpha-numeric pair XN, where X denotes any one of the characters A, B and C, and N denotes any one of the numbers 1, 2, 3, 4 and 5. This is shown in FIG. 2. As one of the three column solid state switches, X, and one of the five row solid state switches, N, is turned on, the heating current selects the path from one pole of the bulk power supply, through one of the three identical pulse current amplifiers, through the column solid state switch X, through the particular actuator XN, and returns through the row solid state switch N to the second pole of the power supply. A single current amplifier used with three column solid state switches would suffice but three current amplifiers are used for the sake of redundancy. Since the current through a series circuit is the same in all the elements of the circuit, individual voltage drops across the solid state switches will have no effect on the actuator current.

Advantages and New Features

The main advantage of the actuation system described here is that it reduces the number of electrical connecting wires required for the actuation of multiple Shape Memory Alloy (SMA) elements. This will prove to be a great advantage when multiple SMA elements will be used as actuators in a miniature device. Miniature devices have space constraints and for SMA actuated miniature devices the number of actuators that can be employed is limited by the number of connecting wires required to power the actuators. Since the articulation capabilities of an active miniature device depends upon the number of actuators, our actuation technique provides a way for enhancing the capabilities of the miniature device by reducing the number of connecting wires.

Alternatives

In our method of actuation, the Shape Memory Alloy (SMA) elements are heated by a current pulse whose amplitude and duration are both variables; they can be chosen to suit our needs. The amplitude of the current can be varied by varying the input to the current amplifier. The duration of the current pulse, whose lower limit depends upon the speed of the computer system being used, can be changed using programming methods.

As a simple variation of our approach, the magnitude of the current pulse can be fixed at some level. The control of the SMA actuators can then be achieved by changing the duration of the pulse. This method would eliminate the need for the variable current amplifiers. Using this method it would still be possible to sense the resistance of the SMA actuators, that can be used for feedback control.

As a second alternative, the duration of the current pulse can be fixed. The duration of the pulse can be fixed by the software or an independent timer, or some combination of the two. In such a situation, the SMA actuators can be controlled by solely varying the magnitude of the current pulse. This method will also provide the scope for feedback control using resistance feedback.

As a third alternative, the control of the SMA active elements can be accomplished by using a separate "free running" timer interface, synced to the voltage sensing multiplexer and the actuator selection circuitry, to drive the on and off periods. This can be done with a constant or a variable current drive and may be accomplished through various "gating" techniques. In this method the computer would have a lower software load.

Obviously many modifications and variations of the present invention are possible in light of the above teachings. It is, therefore, to be understood that the present invention may be practiced within the scope of the following claims other than as specifically described.

What is claimed is:

1. A method of actuating Shape Memory Alloy (SMA) elements, comprising:

wiring SMA elements into a matrix composed of rows and columns;

selecting each SMA element by using a separate free running timer interface, synced to a voltage sensing multiplexer and the actuator selection circuitry, to drive the on and off periods;

cyclically heating each SMA element individually and sequentially by a current pulse;

measuring the changing resistance of each SMA element to adjust the pulse used to heat the element, whereby a device can be controlled for its intended purposes.

2. The method set forth in claim 1 of actuating Shape Memory Alloy elements, wherein:

the current is constant.

3. The method set forth in claim 1 of actuating Shape Memory Alloy elements, wherein:

the current is variable.

4. The method set forth in claim 1 of actuating Shape Memory Alloy elements, wherein:

the current is pulsed through various gating techniques.

* * * * *